United States Patent [19]
Di Rocco et al.

[11] Patent Number: 5,496,836
[45] Date of Patent: Mar. 5, 1996

[54] USE OF FAMOTIDINE AND RELATED COMPOUNDS IN THE TREATMENT OF MOVEMENT DISORDERS

[75] Inventors: Alessandro Di Rocco, New York, N.Y.;
Susan Molinari, River Edge, N.J.;
Ram Kaminski, Riverdale, N.Y.

[73] Assignee: Mount Sinai School of Medicine of the City University of New York, New York, N.Y.

[21] Appl. No.: 238,704

[22] Filed: May 5, 1994

[51] Int. Cl.$^6$ .............................................. A61K 31/425
[52] U.S. Cl. ........................................................ 514/370
[58] Field of Search ................................................ 514/370

[56] References Cited

U.S. PATENT DOCUMENTS

| | | | |
|---|---|---|---|
| 4,757,060 | 7/1988 | Lukacsko et al. | 514/160 |
| 4,806,548 | 2/1989 | Ivanova et al. | 514/310 |
| 5,070,101 | 12/1991 | Kaminski | 514/399 |
| 5,177,081 | 1/1993 | Kaminski | 414/279 |
| 5,352,688 | 10/1994 | Kaminski | 514/357 |

OTHER PUBLICATIONS

Kaminski et al., 1994, New Trends Clin. Neuropharmacol 8:306.
Eisen and Calne, 1992, Can. J. Neurol. Sci. 19:120.
Hill, 1992, Biochemical Society Transactions 20:122–125.
Airaksinen et al., 1991, Neuroscience 44:465–481.
Airaksinen et al., 1991, Agents and Actions 33:104–107.
Sakai et al., 1991, Life Science 48:2397–2404.
Calne and Eisen, 1990, Advances in Neurology 53;83–100.
Martinez–Mir et al., 1990, Brian research 526:322–327.
Ruat et al., 1990, Proc. Natl. Acad. Sci. USA 87:1658–1662.
Beuthenet, 1988, Neuroscience 26:553–560.
O'Neill and Gertner, 1987, Pharmacology Biochemistry and Behavior 26:683–686.
Scwartz et al., 1986, J. Exp. Biol. 124:203–224.
Robert Berkow, "Extrapyramidal and Cerebellar Disorders–Parkinsonism", The Merck Manual of Diagnosis and Therapy, 14th Edition, 1358–1362 (1982).
Cerone et al., "Parkinsonian tremor: a neuropharmacological study", Acta Neurol. belg., vol. 77, pp. 213–229 (1977).
Coelho et al., "Decrease in Blood Histamine in drug–Treated Parkinsonian Patients", Molecular and Chemical Neuropathology, vol. 14, pp. 77–85 (1991).
Garbarg et al., "Brain Histidine Decarboxylase Activity in Parkinson's Disease", The Lancet, pp. 74–75 (1983).
Gelenberg, "Famotidine for Schizophrenia", Biological Therapies in Psychiatry Newsletter, vol. 13, pp. 43–44 (1990).
Heleniak et al., "Histamine Methylation in Schizophrenia", Medical Hypotheses, vol. 30, pp. 167–174 (1989).
Hough et al., "A Role for Histamine and Histamine $H_2$–Receptors in Non–Opiate Footshock–Induced Analgesia", Life Sciences, vol. 36, pp. 859–866 (1985).
Kaminsky et al., "Effect of famotidine on deficit systoms of schizophrenia", The Lancet, vol. 335, pp. 1351–1352 (1990).

Onodera et al., "Pharmacological characteristics of catalepsy induced by intracerebroventricular administration of histamine in mice: The improtance of muscarinic step in central cholinergic neurons", Agents and Actions, vol. 33, pp. 143–146 (1991).

Oyewumi et al., "Famotidine as an Adjunct Treatment of Resistant Schizophrenia", Journal of Psychiatry & Neuroscience, vol. 19, pp. 145–150 (1994).

Poirier et al., "Debrisoquine Metabolism in Parkinsonian Patients Treated with Antihistamine Drugs", The Lancet, p. 386 (1987).

Timmerman, "Histamine Agonists and Antagonists", Acta Otolaryngol (Stockh) Suppln. 479, pp. 5–11 (1991).

Growden et al., "Distinctive Aspects of Cognitive Dysfunction in Parkinson's Disease", Advances in Neurology, vol. 53, 1990, pp. 365–376.

*Primary Examiner*—Marianne M. Cintins
*Assistant Examiner*—William R. A. Jarvis
*Attorney, Agent, or Firm*—Brumbaugh, Graves, Donohue & Raymond

[57] ABSTRACT

The present invention relates to methods of treating movement disorders which comprise administering famotidine or a related compound to a subject in need of such treatment, wherein the motor disorder is selected from the group consisting of olivo-ponto-cerebellar atrophy, multi-system atrophy, Shy-Drager syndrome, kernicterus, Leigh's disease, cerebellar ataxias, neonatal hypoxemia syndromes, carbon monoxide poisoning, progressive supranuclear palsy, tardive dystonias, oculogyral crises, manganese poisoning, Wilson's Disease, Huntington's Disease, striatonigral degeneration, ingestion by the subject of phenothiazines, butyrophenones or reserpine, Alzheimer's Disease, normal pressure hydrocephalus, obstructive hydrocephalus, physiologic tremor, benign familial tremor, cerebellar tremor, rubral tremor, toxic tremor, metabolic tremor, senile tremor, chorea, ballism, athetosis, dystonia, tics, tardive dyskinesia, paroxysmal choreoathetosis, tonic spasm, akathisia, muscle rigidity, postural instability, bradykinesia, difficulty in initiating movements, muscle cramps, dyskinesias, myoclonus, and Creutzfeldt-Jacob Disease, and wherein the subject does not exhibit bradyphrenia. In preferred embodiments of the invention, the movement disorder is associated with an abnormality in basal ganglia structure or function. In a particularly preferred embodiment of the invention, the movement disorder is a component of Parkinson's Disease. The present invention is based, at least in part, on the discovery that Parkinson's Disease patients treated with famotidine reported improved motor function, diminished tremor, and decreased dyskinesias and "on/off" fluctuations in their response to conventional levodopa therapy.

6 Claims, No Drawings

USE OF FAMOTIDINE AND RELATED COMPOUNDS IN THE TREATMENT OF MOVEMENT DISORDERS

INTRODUCTION

The present invention relates to methods of treating movement disorders which utilize famotidine or famotidine-related compounds. It is based, at least in part, on the discovery that famotidine ameliorates the symptoms and signs of Parkinson's Disease. In preferred embodiments of the invention, famotidine or a famotidine-related compound may be used to treat neurological disorders which are associated with abnormalities in basal ganglia structure or function.

BACKGROUND OF THE INVENTION

2.1. NEUROLOGICAL MOVEMENT DISORDERS

Components of the human nervous system which control movement may be classified into the following five categories: (1) "upper" motor neurons located in the cerebral cortex and their fiber projections to "lower" motor neurons in the spinal cord; (2) lower motor neurons in the spinal cord and their fiber projections to neuromuscular junctions; (3) brainstem nuclei which project to the spinal cord and control posture, automatic and repetitive movements; (4) two subcortical systems, namely the basal ganglia and the cerebellum, which control muscle tone, posture, and coordination of movement; and (5) cortical structures, such as the premotor and accessory motor cortex, which are involved in the planning and programming of voluntary movement (Adams and Victor, 1985, *Principles of Neurology*, Third Edition, McGraw-Hill Book Company, New York, pp.35–36). Conditions which disturb the structure and/or function of these components give rise to movement disorders that may be associated with paralysis, lack of coordination, or adventitious movements such as tics and tremor (Id.)

2.2. DISORDERS OF THE BASAL GANGLIA

The term "basal ganglia" refers to a group of subcortical structures which includes the caudate, putamen, globus pallidus, subthalamic nucleus, and substantia nigra (Adams and Victor, 1985, *Principles of Neurology*, Third Edition, McGraw-Hill Book Company, New York, p.53). The caudate, putamen and nucleus accumbens are often considered to be a single structure, referred to as the neostriatum or striatum, in which case the more medial region, which includes the globus pallidus, is termed the palleostriatum or pallidum (Adams and Victor, 1985, *Principles of Neurology*, Third Edition, McGraw-Hill Book Company, New York, p.54).

The basal ganglia, which are interconnected with numerous central nervous system ("CNS") structures, are important for "fine-tuning" movements initiated in the cerebral cortex (Plum and Posner, 1985, "Neurology", reprinted from *Pathophysiology—The Biological Principles Of Disease*, Smith and Thier, eds., W. B. Saunders, Philadelphia, p.1040). The basal ganglia receive a signal from the cerebral cortex before the newly initiated movement begins, integrate the signal with input gathered from other CNS structures, and then return the synthesized information to the cortex, which modulates its instructions regarding the movement (Id.). In this manner, posture, the speed of initiation and continuity of movement, and the ability to perform several tasks at once are controlled.

The important role played by the basal ganglia in motor function may be appreciated by considering the consequences of basal ganglia dysfunction. The manifestations of basal ganglia dysfunction, often referred to as "extrapyramidal symptoms" have been placed in five major categories: (1) dyskinesias including tremor, writhing movements ("athetosis"), distorted posturing ("dystonia"), rapid dance-like movements ("chorea"), and flinging of the extremities ("ballism"); (2) abnormal resistance of muscles to stretching; (3) disorders involving the initiation of movements and in the ability to perform successive motor acts; (4) prominent impairment of midline and other bilaterally innervated movements (e.g., abnormal speech); and (5) abnormal postural control (Plum and Posner, 1985, "Neurology" reprinted from *Pathophysiology—The Biological Principles Of Disease*, Smith and Thier, eds., W. B. Saunders, Philadelphia, p.1066). Two well-known examples of basal ganglia disorders are Parkinson's Disease and Huntington's Chorea.

2.3. PARKINSON'S DISEASE

Parkinson's Disease is a prevalent, serious neurological disorder (afflicting approximately one-half million people in the United States; Bianchine, 1985, in *The Pharmacological Basis of Therapeutics*, Seventh Edition, Gilman et al., eds., Macmillan Publishing Co., New York, p. 473) which is associated with a number of clinical motor symptoms and signs, the most prominent of which are tremor, rigidity, and bradykinesia. The tremor of Parkinson's Disease is most characteristically observed in the patient's hands, which exhibit a distinctive "pill-rolling" movement (Patten, 1983, *Neurological Differential Diagnosis*, Springer-Verlag, New York, pp.125–126). The patient typically demonstrates rigidity in all muscle groups, resulting in stiffness of movement throughout the entire range (Id.). Bradykinesia, a slowing of movements, renders the execution of even the most routine daily tasks difficult or impossible (Id.). The consequent inability to rapidly adjust posture leaves the patient susceptible to tripping and falling (Id.). In addition to the motor symptoms, many Parkinson's Disease patients become depressed or demented (Sano et al., 1989, Arch. Neurol. 46:1284–1286).

The physiological basis for Parkinson's Disease appears to lie in the degeneration of pigmented dopamine-synthesizing cells in the pars compacta of the substantia nigra (Plum and Posner, 1985 "Neurology", reprinted from *Pathophysiology—The Biological Principles Of Disease*, Smith and Thier, eds., W. B. Saunders, Philadelphia, p.1067). Although sometimes the result of exposure to toxins, in most instances, the cause of this degeneration is unknown (Id.) The loss of dopamine-producing cells has a profound impact on motor function because many neurons within the basal ganglia utilize dopamine as a neurotransmitter (Id.). Most current therapies for Parkinson's Disease attempt to compensate for this loss of dopamine-producing cells.

The cornerstone of Parkinson's Disease treatment has been dopamine replacement therapy, in which levodopa (L-3, 4-dihydroxyphenylalanine) is administered together with an inhibitor of peripheral dopa decarboxylase enzyme (for example, carbidopa), which permits dopamine to cross the blood brain barrier in sufficient quantities. While levodopa therapy is initially beneficial to most Parkinson's Disease patients, its therapeutic effectiveness often declines after long-term treatment (Ludin and Bass-Verry, 1976, J. Neural Transm. 38:249–258). In particular, fluctuations in the response of motor symptoms to therapy ("on-off" phenomena; Marsden and Parkes, 1976, Lancet 1:292–296; Lewitt and Chase, 1983, Trends Neurosci. 6:1) and drug-induced psychosis (Goodwin, 1971, JAMA 218:1915–1920) occur with relative frequency. While a number of agents, including bromocriptine, lisuride, amantadine, apomorphine, selegiline, trihexyphenidyl, benztropine mesylate, procyclidine hydrochloride, biperiden hydrochloride, ethopropazine hydrochloride, diphenhydramine hydrochloride, orphenadrine hydrochloride and pergolide have been used with varying success, none of these medications has proved to be completely satisfactory, and a better agent for treating the symptoms of Parkinson's Disease, which would provide continuous relief of symptoms without substantial adverse side effects has been sought (Akai et al., 1993, Ann. Neurol. 33:507–511).

2.4. HISTAMINE RECEPTORS IN THE BRAIN

Three species of histamine receptor have been identified in the brain, and are referred to as $H_1$, $H_2$, and $H_3$ receptors. $H_1$ and $H_2$ receptors appear to occur in a number of tissues. $H_1$ receptors are coupled to inositol phospholipid hydrolysis, and are associated with a variety of functional responses, including smooth muscle contraction, increased vascular permeability, hormone release and cerebral glycogenolysis (Hill, 1992, Biochem. Soc. Transac. 20:122–125). $H_2$ receptors are positively coupled to adenylate cyclase and stimulate the formation of intracellular cyclic AMP, and are associated with gastric acid secretion, smooth muscle relaxation, cardiac muscle effects, and inhibition of lymphocyte function (Id.). $H_3$ receptors are found in both the central and peripheral nervous systems, and regulate the release of a range of neurotransmitter substances. Whereas $H_1$ and $H_2$ receptors in the nervous system are postsynaptically distributed, $H_3$ receptors are localized presynaptically (Schwartz et al., 1986, J. Exp. Biol. 124:203–224).

The regional distribution of these receptors in the brain has been studied using radiolabelled, receptor-specific ligands. In particular, when radiolabelled iodobolpyramine, which binds to $H_1$ receptors; radiolabelled iodoaminopotentidine, which binds to $H_2$ receptors; and radiolabelled (R)α-methylhistamine, which binds to $H_3$ receptors, were incubated with sections of human or monkey brain, the following results were obtained (as described in Martinez-Mir, 1990, Brain Res. 526:322–327). High densities of $H_1$ receptors were observed in the most internal layers of the neocortex, claustrum, hippocampal formation and thalamus, and, perhaps nonspecifically, in the globus pallidus. $H_2$ receptors were detected predominantly in the basal ganglia (in particular the caudate, putamen and accumbens nuclei), and to a somewhat lesser extent in the superficial layers of cerebral cortex, claustrum, globus pallidus, and hippocampal formation. $H_3$ receptors were found to be particularly concentrated in the globus pallidus, caudate, putamen, and hippocampus, and, to a somewhat lesser extent, the external layers of the cortex. In human, monkey, and guinea pig brain, $H_1$ receptors appeared to be particularly abundant in the neocortex whereas $H_2$ and $H_3$ receptors were observed to be enriched in the basal ganglia. It was suggested that drugs acting at these sites may influence the control of motor functions.

Studies performed to evaluate the effects of centrally administered $H_2$ receptor antagonists on motor activity, performed in mice, indicated that two structurally distinct $H_2$ receptor antagonists, cimetidine and BMY 25,368, reduced locomotor activity (O'Neill and Gertner, 1987, Pharmacol., Biochem. Behavior 26:683–686). Similarly, Sakai et al. (1991, Life Sci. 48:2397–2404) reported that a $H_3$ antagonist, thioperamide, increased locomotor activity in mice (presumably by promoting histamine release) but that this increase could be blocked by pretreatment with either an $H_1$ or $H_2$-receptor antagonist (pyrilamine or zolantidine, respectively). A role of histamine in arousal is suggested (O'Neill and Gertner, 1987, Pharmacol., Biochem. Behavior 26:683–686; Sakai et al., 1991, Life Sci. 48:2397–2404).

Antihistamine compounds, such as diphenhydramine hydrochloride and orphenadrine hydrochloride, antagonists which act at the $H_1$ histamine receptor, have been used to treat Parkinson's disease (Garbarg et al., 1983, Lancet Jan. 1/8, p.74–75; Yahr and Duvoisin, 1972, N. Engl. J. Med. 287:20). These drugs have been found to demonstrate limited efficacy (Bianchine, 1985, in *The Pharmacological Basis of Therapeutics*, Seventh Edition, Gilman et al., eds., Macmillan Publishing Co., New York, p. 484).

Because $H_1$ receptor antagonists have been used in the treatment of Parkinson's Disease (Yahr and Duvoisin, 1972, N. Engl. J. Med. 287:20), the levels of histidine decarboxylase, the specific synthesizing enzyme of histamine, were measured in Parkinson's Disease patients and compared with levels in normal controls (Garbarg et al., January ⅛, 1983, Lancet pp. 74–75). The amount of histidine decarboxylase activity in Parkinson's Disease patients was found not to significantly differ from activity measured in normal controls, suggesting that histaminergic neurotransmission may not be affected and that, therefore, $H_1$ antihistaminics might still improve parkinsonian symptoms by reducing histamine neurotransmission (Id.).

2.5. PRIOR USES OF FAMOTIDINE AND RELATED COMPOUNDS

Famotidine and related compounds such as cimetidine and ranitidine are antagonists of the $H_2$ receptor for histamine, and, as such, suppress gastric acid secretion. They are widely used in the treatment and prevention of gastric and duodenal ulcers, gastritis, reflux gastroesophagitis, gastrointestinal bleeding and pulmonary aspiration of acid (Langtry et al., 1989, Drugs 38: 551– 590), and are associated with a low incidence of adverse reactions which, when they do occur, are generally minor (Douglas, 1985, in *The Pharmacological Basis of Thereapeutics*, Seventh Edition, Gilman et al., eds., Macmillan Publishing Co., New York, p. 626). More recently, these compounds, particularly famotidine, have been found to be useful as psychopharmaceutical agents in the treatment of the so-called negative symptoms of schizophrenia (see, for example, U.S. Pat. No. 5,177,081 by Kaminski, issued Jan. 5, 1993) and apathy-amotivation ("bradyphrenia") of Parkinson's Disease (Kaminski et al., 1994, New Trends Clin. Neuropharmacol., 8:306; U.S. patent application Ser. No. 07/954,258). No motor effects of these compounds had been documented prior to the present invention.

3. SUMMARY OF THE INVENTION

The present invention relates to methods of treating movement disorders which comprise administering famotidine or a famotidine-related compound to a subject in need of such treatment. In preferred embodiments of the invention, the movement disorder is associated with an abnormality in basal ganglia structure or function. In a particularly preferred embodiment of the invention, the movement disorder is a component of Parkinson's Disease. The present invention is based, at least in part, on the discovery that Parkinson's Disease patients treated with famotidine reported improved motor function, diminished tremor, and decreased "on/off" fluctuations in their response to conventional levodopa therapy.

4. DETAILED DESCRIPTION OF THE INVENTION

For purposes of clarity of disclosure, and not by way of limitation, the detailed description of the invention is divided into the following subsections:

(i) famotidine and famotidine-related compounds;
(ii) movement disorders; and
(iii) treatment regimens.

4.1. FAMOTIDINE AND FAMOTIDINE-RELATED COMPOUNDS

The present invention employs famotidine or famotidine-related compounds in the treatment of movement disorders, particularly those which are associated with abnormalities in basal ganglia structure or function.

Famotidine, has the following structural formula:

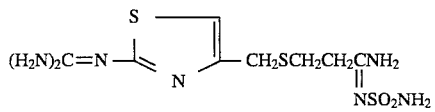

and may be obtained under the trade name Pepcid.

The term "famotidine-related compounds", as used herein, refers to compounds which are structurally or functionally related to famotidine.

Structurally related compounds include enantiomers, isomers, analogs and derivatives of famotidine and compounds having structural formulas which exhibit substantial similarity to the structural formula of famotidine, as set forth above. For example, but not by way of limitation, a famotidine related compound may belong to the guanidinothiazole group of compounds.

Compounds which are functionally related to famotidine include other $H_2$ antagonists, including but not limited to ranitidine, cimetidine, nizatidine, omeprazole, tiotidine, zolantidine, aminofurazan compounds and ORF 17578.

In certain non-limiting embodiments, famotidine-related compounds which may be used according to the invention may be identified by testing the ability of the compound to compete with famotidine for binding to a histamine receptor and/or to bind to brain tissue, and preferably basal ganglia tissue. For example, the techniques for evaluating the binding of histamine agonists and antagonists to brain tissue are well known (Schwarz et al., 1986, J. Exp. Biol. 124: 203–224; Bouthenet, 1988, Neuroscience 26:553–600; Martinez-Mir, 1990, Brain Res. 526:322–327). Such techniques could be used to evaluate, for example, the ability of a putative famotidine-related compound to compete with radiolabelled famotidine for in situ binding to basal ganglia tissue. The ability to compete successfully with famotidine for binding sites (with either a stronger or weaker binding affinity compared to famotidine) would identify a compound as being famotidine-related.

For example, and not by way of limitation, a famotidine-related compound may be identified by demonstrating the ability of the compound to inhibit the binding of radiolabelled famotidine or the binding of $[^{125}I]$ iodoaminopotentidine to brain tissue, particularly to basal ganglia tissue. According to the latter embodiment, preparations of brain tissue, preferably human brain tissue, may be preincubated in 50 mM $Na_2/K$ phosphate buffer, pH 7.4, at room temperature, followed by a 3 hour incubation at room temperature in the same buffer to which either 0.05 nM $[^{125}I]$ iodoaminopotentidine alone, or in combination with various concentrations of putative famotidine-related compound, has been added. Non-specific $H_2$ binding may be determined by incubating consecutive tissue sections in the presence of 3 μM tiotidine. If the presence of putative famotidine-related compound decreases the amount of radioactivity bound, preferably in a dose-dependent manner, the compound may be considered to be famotidine related. Alternatively if, in analogous experiments which utilize radiolabelled famotidine, the presence of putative famotidine-related compound decreases the amount of radioactivity bound, preferably in a dose-dependent manner, then the compound may be considered to be famotidine-related. See, for example, Martinez-Mir, 1990, Brain Res. 526:322–327.

4.2. MOVEMENT DISORDERS

The present invention may be used to treat movement disorders, and in particular movement disorders associated with abnormalities in basal ganglia structure and/or function. Such movement disorders include, but are not limited to, the following.

The present invention may be used in the treatment of (i) tremor, including, but not limited to, the tremor associated with Parkinson's Disease, physiologic tremor, benign familial tremor, cerebellar tremor, rubral tremor, toxic tremor, metabolic tremor, and senile tremor; (ii) chorea, including, but not limited to, chorea associated with Huntington's Disease, Wilson's Disease, ataxia telangiectasia, infection, drug ingestion, or metabolic, vascular or endocrine etiology (e.g., chorea gravidarum or thyrotoxicosis); (iii) ballism (defined herein as abruptly beginning, repetitive, wide, flinging movements affecting predominantly the proximal limb and girdle muscles); (iv) athetosis (defined herein as relatively slow, twisting, writhing, snake-like movements and postures involving the trunk, neck, face and extremities); (v) dystonia (defined herein as a movement disorder consisting of twisting, turning tonic skeletal muscle contractions, most, but not all of which are initiated distally); (vi) paroxysmal choreoathetosis and tonic spasm; (vii) tics (defined herein as sudden, behaviorally related, irregular, stereotyped, repetitive movements of variable complexity); (viii) tardive dyskinesia; (ix) akathesia, (x) muscle rigidity, defined herein as resistance of a muscle to stretch; (xi) postural instability; (xii) bradykinesia; (xiii) difficulty in initiating movements; (xiv) muscle cramps; (xv) dyskinesias and (xvi) myoclonus.

The present invention may be used in the treatment of disorders with extrapyramidal symptoms and signs, including, but not limited to, olivo-ponto-cerebellar atrophy, multisystem atrophy, Shy-Drager syndrome, kernicterus, Leigh's disease, cerebellar ataxias, neonatal hypoxemia syndromes, carbon monoxide poisoning, progressive supranuclear palsy, tardive dystonias, oculogyral crises, manganese poisoning, Wilson's Disease, Huntington's Disease, striatonigral degeneration and conditions associated with the ingestion of compounds such as phenothiazines, butyrophenones, and reserpine.

In a preferred, non-limiting embodiment, the present invention may be used to treat the motor symptoms of Parkinson's Disease, including, but not limited to, tremor, bradykinesia, rigidity, difficulty in initiating movements and postural instability. The term "Parkinson's Disease, as used herein, refers to conditions having the clinical features set forth above in Section 2.3, regardless of the pathogenesis. Advantageously, the present invention may be used to reduce the "on-off" phenomena and dyskinesias associated with conventional levodopa therapy.

The present invention may also be used in the treatment of the motor symptoms of Alzheimer's Disease, normal pressure and obstructive hydrocephalus, and Creutzfeldt-Jacob Disease.

4.3. TREATMENT REGIMENS

The present invention provides for methods of ameliorating a motor symptom in a subject suffering from a movement disorder, as set forth in the preceding section, comprising administering, to the subject, a therapeutically effective amount of famotidine or a famotidine-related compound, as set forth in section 4.1.

The phrase "ameliorating a motor symptom" refers to either subjective or objective improvement of a motor symptom, and does not require that the motor symptom be eliminated completely. Rather, the motor symptom may be rendered reduced to an extent that is noticeable by the subject or a clinician. Preferably, the reduction results in an improvement in the quality of life of the subject.

Further, the present invention provides for a method of reducing the occurrence of "on-off" phenomena in a person suffering from Parkinson's Disease, comprising administering, to the subject, a therapeutically effective amount of famotidine or a famotidine-related compound. The phrase "reducing the occurrence", as used herein, refers to reducing either the frequency or severity of "on-off" phenomena or of increasing the time interval between fluctuations.

The subject may be a human or non-human subject.

A therapeutically effective amount is defined herein as an amount which ameliorates the motor symptoms and signs associated with a movement disorder or which reduces the occurrence of "on-off" phenomena in a patient suffering from Parkinson's Disease. Such dosage may vary from patient to patient, depending on the movement disorder being treated, the physical characteristics of the patient, the route of administration, and, where, a famotidine-related compound is being utilized, the potency and bioavailability of the compound, but may be ascertained using routine techniques, such as those described in Benet and Sheiner, Ross and Gilman, and Blaschke et al., 1985, in *The Pharmacological Basis of Therapeutics*, Seventh Edition, Gilman et al., eds., Macmillan Publishing Co., New York pp. 3–65. For example, if a subject is suffering from tremor, the subject may first be administered a low dosage of famotidine or a famotidine-related compound; if the patient's tremor is eliminated, the dosage may be maintained or reduced, but if the tremor is unchanged or insufficiently lessened, then the dosage may be incrementally increased until the tremor is reduced or until a therapeutic ceiling has been reached.

According to the invention, famotidine or famotidine-related compound may be administered as a sole agent for the treatment of the motor disorder or in conjunction with another agent or agents. Such agents include, but are not limited to, levodopa, carbidopa, combinations of carbidopa and levodopa (e.g. trade name Sinemet), bromocriptine mesylate (e.g. trade name Parlodel), lisuride, pergolide mesylate (e.g. trade name Permax), selegiline hydrochloride (e.g. trade name Eldepryl), trihexyphenidyl hydrochloride (e.g. trade name Artane), benztropine mesylate (e.g. trade name Cogentin), orphenadrine citrate (e.g. trade name Norflex), Parsitan, Madopar, Benserazide, apomorphine, biperiden hyrochloride and biperiden lactate (e.g. trade name Akineton), diphenhydramine hydrochloride (e.g. trade name Benadryl), procyclidine hydrochloride (e.g. trade name Kemadrin), hyoscyamine sulfate (e.g. trade name Levsin), Ropinirole, Tolcapone, amantidine hydrochloride (e.g. trade name Symmetrel), cabergoline, other dopaminergic agonists, MAO-inhibitors, growth factors, COMT-inhibitors.

In particular, non-limiting embodiments of the invention, an initial dose of between 20–160 mg famotidine, or an equivalent amount of famotidine-related compound, may be administered per day to a patient suffering from a movement disorder. In preferred embodiments of the invention, the initial dose may be between 40–80 mg famotidine, or an equivalent amount of a famotidine-related compound, administered orally per day. An equivalent amount of a famotidine-related compound refers to an amount of the famotidine-related compound having essentially the same functional activity as the specified amount of famotidine. The determination of what constitutes an "equivalent amount" of a famotidine-related compound may take into consideration how the potency and bioavailability of the famotidine-related compound compares to the potency and bioavailability of famotidine. For example, if a famotidine-related compound has twice the potency and the same bioavailability characteristics as famotidine, then if an initial dose of between 20–160 mg per day famotidine is recommended, the recommended initial dose of the famotidine-related compound would be 10–80 mg per day. The term "bioavailability", as used herein, refers to the extent to which a drug reaches its site of action or a biological fluid from which the drug has access to its site of action, as set forth in Benet and Sheiner, 1985, in *The Pharmacological Basis of Therapeutics*, Seventh Edition, Gilman et al., eds., Macmillin Publishing Co., New York, p. 5.

Further, according to this same particular non-limiting embodiment of the invention, the subject may then be observed for several weeks to determine whether his or her motor symptom or symptoms have improved. If they have improved substantially, it is preferred that the initial dose of famotidine or famotidine-related compound be maintained. If the motor symptom or symptoms have not shown any improvement, then the dose of famotidine or famotidine-related compound may be increased by between 50–100 percent, again, taking into consideration the characteristics of the particular subject being treated. If, alternatively, the motor symptom or symptoms have improved somewhat, but not to a sufficient extent, then the dose of famotidine or famotidine-related compound may be increased by between 25– 100 percent. The patient may then be reevaluated after several weeks, and the dose again adjusted, as set forth above. This process may be repeated until the desired therapeutic effect is obtained. The amount of famotidine administered may be increased to a maximum dose of about 600 mg or until serious side effects appear. The maximum dose of famotidine-related compound may be equivalent but also may vary depending on the specific characteristics of the compound.

In a preferred, non-limiting embodiment of the invention, an initial daily dose of between 40–80 mg oral famotidine, or an equivalent amount of famotidine-related compound, is administered to a human subject suffering from Parkinson's disease, in conjunction with that subject's previous treatment regimen (for example, but not by limitation, in addition to, that subject's levodopa treatment regimen). If the subject is not yet receiving other anti-Parkinsonism medication, then it may be appropriate to administer famotidine as the sole therapeutic agent. After several weeks, the motor symptoms and signs of the subject may be reevaluated. If the symptoms and signs have not improved, the dose may be increased by between 50–100%. If the symptoms and signs have not improved sufficiently, the dose may be increased by between 25–100%. The subject may then be again evaluated in several weeks, and the process repeated until the desired therapeutic effect is achieved. Maximum doses are as described above.

In further embodiments of the invention, famotidine or famotidine-related compound may be administered subcutaneously, intramuscularly, intranasally, by inhalation, intravenously, intraperitoneally, intrathecally, or rectally. Famotidine or famotidine-related compound may also be administered via sustained release microparticles or implants. In addition, the dosing intervals may be adjusted to meet the needs of a particular subject and multiple doses per day may be administered.

5. EXAMPLE: FAMOTIDINE DECREASED MOTOR SYMPTOMS OF PARKINSON'S DISEASE

Four patients suffering from Parkinson's Disease were treated according to the invention with 80 mg/day of famotidine, administered orally.

Prior to and during famotidine treatment, the patients were treated with the following medications:

Patient No. 1 was treated with Symmetrel, 100 mg twice daily; Eldepryl, 5 mg twice daily, and Sinemet 25/100, ½ tablet five times daily.

Patient No. 2 was treated with Cogentin, 1 mg twice daily; Eldepryl, 5 mg twice daily; and Sinemet 25/100, one tablet three times daily.

Patient No. 3 was treated with Cogentin, 1 mg twice daily; Nortryptyline 25 mg before sleep; Eldepryl 5 mg twice daily; CR-Sinemet (50/200), ½ tablet daily; and Sinemet 25/100, one tablet five times daily.

Patient No. 4 was treated with Betoptic eye drops 0.25% to both eyes four times daily; Eldepryl 5 mg twice daily; and Sinemet 25/100, one tablet four times daily.

About 2–3 weeks after famotidine treatment had been initiated, the following improvements in the motor symptoms of the patients were noted. Evaluation of motor symptoms was by standard neurological clinical examination.

In Patent No. 1, tremor had nearly disappeared, on/off fluctuations had virtually disappeared, rigidity had improved, and dyskinesias had significantly improved. These clinical improvements have persisted for fifteen months to date.

In Patient No. 2, tremor had significantly improved. This improvement continued for three months of famotidine therapy, at which point treatment was stopped for reasons unrelated to the patient's Parkinson's Disease.

In Patient No. 3, tremor and on/off fluctuations had virtually disappeared, rigidity had improved and dyskinesias had significantly improved. These improvements have persisted for one year of famotidine therapy, except that a slight amount of tremor has reappeared.

In Patient No. 4, tremor improved. This patient has been lost to follow-up.

In neither patient who continues in the famotidine study has the stage of Parkinson's Disease advanced, an observation atypical of the standard course of the disease.

Various publications are cited herein, each of which is hereby incorporated by reference in its entirety.

What is claimed is:

1. A method for ameliorating a motor symptom in a subject wherein the motor symptom is caused by a disorder selected from the group consisting of olivo-ponto-cerebellar atrophy, multi-system atrophy, Shy-Drager syndrome, kernicterus, Leigh's Disease, cerebellar ataxias, neonatal hypoxemia syndromes, carbon monoxide poisoning, progressive supranuclear palsy, tardive dystonias, oculogyral crises, manganese poisoning, Wilson's Disease, Huntington's Disease, striatonigral degeneration, ingestion by the subject of phenothiazines, butyrophenones or reserpine, Alzheimer's Disease, normal pressure hydrocephalus, physiologic tremor, benign familial tremor, cerebellar tremor, rubral tremor, toxic tremor, metabolic tremor, senile tremor, chorea, ballism, athetosis, dystonia, tics, tardive dyskinesia, paroxysmal choreoathetosis, tonic spasm, akathisia, muscle rigidity, postural instability, bradykinesia, difficulty in initiating movements, muscle cramps, dyskinesias, myoclonus and Creutzfeldt-Jacob Disease, and wherein the subject does not suffer from Parkinson's Disease, comprising administering, to the subject, a therapeutically effective amount of famotidine or a famotidine-related compound.

2. The method according to claim 1, in which the motor symptom is tremor.

3. The method according to claim 1, in which the motor symptom is bradykinesia.

4. The method according to claim 1, in which the motor symptom is postural instability.

5. The method according to claim 1, in which the motor symptom is muscle rigidity.

6. The method according to claim 1, in which the motor symptom is chorea.

* * * * *

UNITED STATES PATENT AND TRADEMARK OFFICE
CERTIFICATE OF CORRECTION

PATENT NO. : 5,496,836

DATED : May 5, 1994

INVENTOR(S) : Di Rocco et al.

It is certified that error appears in the above-indentified patent and that said Letters Patent is hereby corrected as shown below:

<u>Abstract, 11th-from-bottom line</u>, "and Creutz-feldt-Jacob Disease" should read --Creutzfeldt-Jacob Disease, and Parkinson's Disease--;

<u>Col. 8, line 4</u>, "hyrochloride" should read --hydrochloride--.

Signed and Sealed this

Twenty-fourth Day of September, 1996

Attest:

BRUCE LEHMAN

Attesting Officer        Commissioner of Patents and Trademarks